United States Patent [19]

Kauvar et al.

[11] Patent Number: 5,674,688

[45] Date of Patent: *Oct. 7, 1997

[54] METHOD FOR ANALYTE CLASSIFICATION BY SC PROFILES

[75] Inventors: Lawrence M. Kauvar, San Francisco, Calif.; Stuart M. Ambler, Longmont, Colo.

[73] Assignee: Terrapin Technologies, Inc., San Francisco, Calif.

[*] Notice: The term of this patent shall not extend beyond the expiration date of Pat. No. 5,338,659.

[21] Appl. No.: 129,413

[22] Filed: Sep. 29, 1993

Related U.S. Application Data

[63] Continuation-in-part of Ser. No. 678,849, Apr. 2, 1991, Pat. No. 5,338,659 and PCT/US92/02716, Apr. 2, 1992, published as WO92/17784, Oct. 15, 1992.

[51] Int. Cl.$^6$ .................................................. G01N 33/53
[52] U.S. Cl. .................. 435/7.1; 435/7.4; 435/975; 436/501; 436/518; 436/808; 436/815
[58] Field of Search ................... 435/7.1, 7.4, 973; 436/501, 518, 808, 815

[56] References Cited

U.S. PATENT DOCUMENTS

| | | | |
|---|---|---|---|
| 5,217,869 | 6/1993 | Kauver | 435/7.9 |
| 5,300,425 | 4/1994 | Kauver | 435/7.9 |
| 5,338,659 | 8/1994 | Kauver et al. | 435/7.1 |

FOREIGN PATENT DOCUMENTS

| | | |
|---|---|---|
| WO 86/00991 | 2/1986 | WIPO. |
| 8903430 | 4/1989 | WIPO. |

OTHER PUBLICATIONS van Emon, J.N., et al., "Immunoassay Techniques for Pesticide Analysis" Analytical Methods for Pesticides and Plant Growth Regulators: Advanced Analytica Techniques, Sherma J. ed., Academic Press, New York (1989) 217–263.

Vanderlaan, M., et al., "Environmental Monitoring by Immunoassay" Environ Sci Technol (1988) 22:247–254.

Newsome, W.H., "Potential and Advantages of Immunochemical Methods for Analysis of Foods" J Assoc Offic Anal Chem (1986) 69:919–923.

Cheung, Peter Y.K. et al., Analytica Chimica Acta, 282 (1993) 181–192, Harnessing immunochemical cross–reactivity: use of pattern recognition to classify molecular analogs.

Kauvar, L.M. et al., Abstracts of Papers of the American Chemical Society; Harnessing immunochemical cross–reactivity by the use of pattern recognition methods, vol. 203 —The Whole Abstract.

Robinson et al Cytometry 13 pp. 75–82 (1992).

Mannervik et al. PNAS 82 pp. 7202–7206 (1985).

*Primary Examiner*—Lora M. Green
*Attorney, Agent, or Firm*—Morrison & Foerster LLP

[57] ABSTRACT

The precision of identification of analyte composition in a sample, where the possible analytes each provide a series of values for characteristic parameters; in particular where the parameters are generated by cross-reaction with specific binding reagents, is enhanced by applying pattern recognition techniques. Samples to be tested are evaluated with respect to each survey parameter to obtain a pattern of parameter values with respect to each analyte at a given concentration. In the case of the use of a panel of specific binding reagents, the samples to be tested are reacted with this panel and the affinities at various analyte concentrations are determined. This results in a databank of "SC profiles" for known concentrations of each analyte. This databank is stored in a computationally accessible form, which then can be matched against SC profiles obtained by testing unknown samples.

19 Claims, 4 Drawing Sheets and allow mixtures of closely related substances to be analyzed. The method depends on finding a group of reagents, typically antibodies, which show a characteristic pattern of reactivity with each member of the group of possible analytes that may be contained in a sample. The determination of the pattern of reactivity of a panel of reagents against a specific analyte or against a defined mixture of analytes results in the standard survey of characteristic (SC) profile for that analyte or mixture. A plurality of such standard profiles is determined, and the SC profile of the unknown sample is compared with the standard profiles to determine the composition of the sample.

METHOD FOR ANALYTE CLASSIFICATION BY SC PROFILES

This application is a continuation-in-part of U.S. application Ser. No. 07/678,849, filed Apr. 2, 1991, now U.S. Pat. No. 5,338,659, and this application corresponds with PCT/US92/02716, filed Apr. 2, 1992.

TECHNICAL FIELD

The invention relates to analysis of unknown samples using specific binding reagent-based assays. More specifically, the invention concerns the use of pattern recognition, wherein patterns are determined by reactivity of known samples with panels of specific binding reagents, to identify the analyte composition of unknown samples. The method can also recognize classes of analytes.

BACKGROUND ART

Immunoassay and related techniques have become the norm for determination of various analytes in biological samples. A variety of formats designed to simplify and improve the accuracy of these tests is available in the art, and the number represented by this variety of formats is very high.

The success of these assays rests in the ability to provide specific binding reagents, usually antibodies or fragments of antibodies, which are highly specific for the target analyte with respect to additional possible components of the sample. For example, there are a large number of assays on the market for pregnancy which rely on the detection of human chorionic gonadotropin (HCG) in urine. These assays are capable of HCG detection because the antibodies provided, which are immunoreactive with HCG, do not react to any detectable extent with other urinary components.

In certain other contexts, however, it is desired to analyze samples for analytes which are members of groups that are cross-reactive with antibodies prepared against any one of them, and any or a number of which may be present in the same sample. One example of this problem relates to the efforts to determine pesticides and herbicides in the environment, since many of these materials are structurally similar. See, for example, van Emon, J. N., et al., in "Analytical Methods for Pesticides and Plant Growth Regulators: Advanced Analytical Techniques," Sherma, J., ed., Academic Press, New York, 1989, pp. 217–263; Vanderlaan, M., et al., *Environ Sci Technol* (1988) 22:247–254; Newsome, W. H., *J Assoc Offic Anal Chem* (1986) 69:919–923.

Typically, it will not be known for certain which of the several members of a particular class of pesticides, for example the carbamate pesticides, will be present in the environment; in addition, degradation products of the pesticide actually applied may also cross-react with a purportedly specifically immunoreacting antibody or other binding agent. Thus, it will not be possible, in a simple single antibody assay to obtain a reliable picture of the composition of the sample. Indeed, the results of such assays are often given in terms of "equivalents" of a particular identified member of the class to which the antibody, for example, has been prepared. In addition to the cross-reactivity of the possible analytes for any specific binding reagent created against one of them, the concentration ranges of these compounds are very low in typical determinations, typically 10–100 nM, or in the parts per billion range. At these low concentrations, problems of cross-reactivity with more abundant materials are particularly troublesome.

Because of the cross-reactivity discussed above, it is difficult to make a definitive determination of analyte concentration. For example, suppose an antibody has 100 times the affinity for analyte B as for analyte A. It would not be possible to distinguish, using a single determination with that antibody, a 50 nM concentration of analyte A from a 0.5 nM concentration of analyte B. Various mixtures of A and B would also react in a quantitatively identical manner. Thus there is no mechanism to use a single antibody for assaying samples that contain mixtures of various structurally similar analytes.

The present invention overcomes these difficulties by utilizing mathematical pattern recognition techniques applied to panels of information channels for parameter values, such as reaction with reactive agents with overlapping specificities. Once a set of standard profiles for target analytes is determined, more reliable determination of analyte composition in experimental samples becomes possible with concomitant improvement in the accuracy of analyte quantitation.

DISCLOSURE OF THE INVENTION

Methods are provided which permit determination of analyte composition of samples where the potential analytes are closely structurally related. These methods take advantage of pattern recognition techniques and the manipulation thereof to provide detailed information as to sample composition.

In one aspect, the invention is directed to a method to determine the analyte composition of a sample, which method comprises contacting the sample with a panel of specifically reactive reagents each of which is reactive to some differing degree with the members of a class of suspected analytes. A profile of reactivity or a "survey of characteristics (SC)" profile is obtained for the sample, and this SC profile is then matched with a predetermined SC profile of standard known compositions.

In another aspect, the invention is directed to a method to obtain the predetermined SC profile for various known analyte compositions which comprises contacting a set of predetermined compositions with a panel of n reagents reactive with these analytes, preferably reagents that specifically bind these analytes, wherein n is preferably 2–10, and plotting the obtained profile in n-dimensional space for each composition. In still another aspect, the invention is directed to the composition pattern so determined.

In still another aspect, the invention is directed to the use of multi-parametric statistical techniques to define which of the n dimensions have the greatest information content relative to the assay and thus permits selection of the minimum number of characteristics (dimensions) to be measured.

MODES OF CARRYING OUT THE INVENTION

Figure 1A:
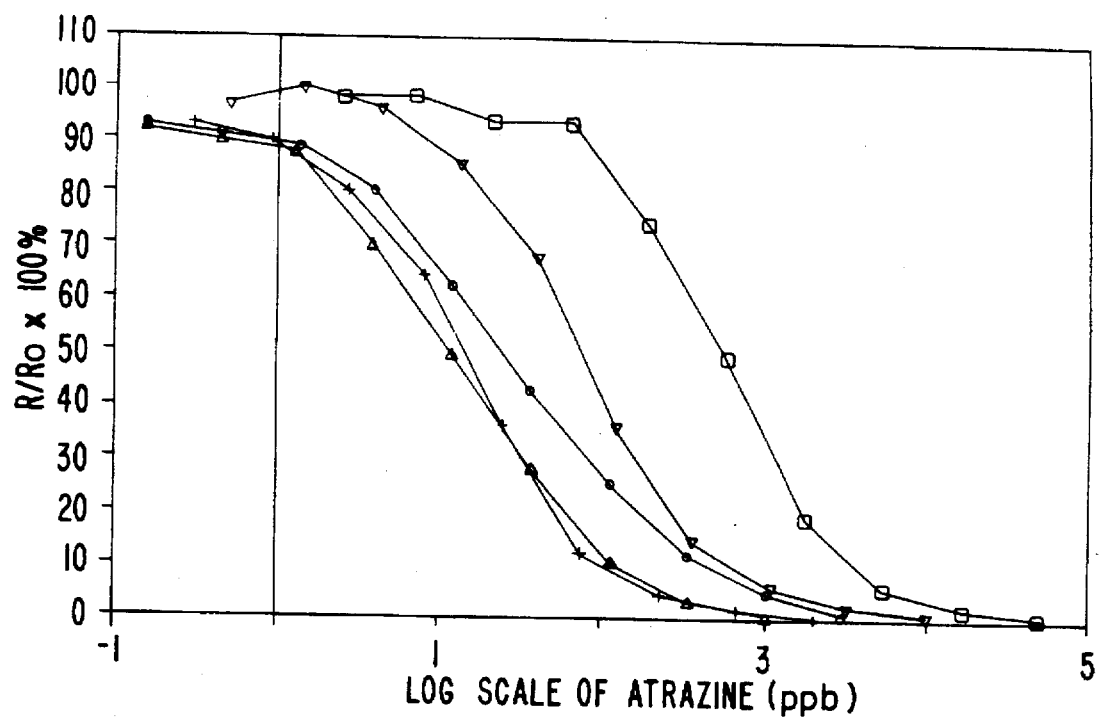
FIG. 1(A) and 1(B) show patterns of inhibition of binding to an immobilized triazine of a series of monoclonal antibodies as a function of concentration of related antigens in solution.

The methods of the invention improve the reliability of determination of analyte compositions in impure samples especially wherein the analytes suspected of being contained in the samples are relatively closely related structurally. By "determination of analyte composition" is meant the ascertainment of the concentration level of each of a number of possible suspected analytes. Situations wherein determination of analyte composition is meaningful include those wherein a number of structurally related materials can be used for similar purposes or where these materials are manipulated in such a way so as to result in their occupying similar environments. For example, many herbicides and pesticides are homologs or analogs of each other, as are their degradation products. Exemplified below is the case of various triazine derivatives, all of which are useful as herbicides.

Other examples of such groups include families of substances which might be found in biological fluids or tissues (useful in clinical analysis of biological samples). In general, these families fall into three categories. First, naturally-occurring substances which may be at enhanced or reduced elevation due to clinical conditions or their direct administration, such as steroids, protein hormones, or metabolites are of interest clinically. Second, artificial materials which are designed for therapeutic purposes, such as beta-blockers, chemotherapeutic agents, prostaglandin inhibitors, and the like, can be monitored. Third, families of various illicit drugs can be detected and distinguished for forensic purposes.

The series of starting reagents and products in a series of reactions leading to the synthesis of a desired product can also be measured (useful in online quality control routines). The method of the invention for such measurement is particularly useful in instances where the materials are synthesized in families and the products represent concomitantly produced and subsequently separated fractions. Typical examples include textile dyes, PCB's used in insulators, and detergents. In all manufacturing, moreover, competing side reactions often produce members of the same family which are structurally similar and need to be distinguished from the desired product.

Analyses related to degradation of various substances in the environment can also be determined (as in the assessment of persistence of environmentally important substances).

The methods of the invention depend on the differential reactivity of the analytes with a set of reagents or other parameters that characterize the analytes. In particular, binding reagents are preferred. Because the analytes are structurally similar, considerable cross-reactivity is expected, and, indeed, the necessity for, and practicality of, the method of the invention depends on this cross-reactivity. While a convenient parameter involves reactivity with a binding reagent, such as an antibody, typically a monoclonal antibody, this is merely an illustration and not a requirement. For example, any substance which is determined to react generally with the group of analytes whose presence, absence or quantity is to be determined is usable in the method of the invention. Antibodies, including, for example, single chain antibodies and recombinantly produced antibodies, can be used per se, or as immunologically reactive fragments thereof, as is well understood in the art. The use of, for example, Fab, Fab' or F(ab')$_2$ fragments is often convenient in specific binding assays. Any reagent interaction which provides suitable cross-reactivity can be used, such as enzyme-substrate or enzyme-inhibitor binding, ligand-receptor binding, or binding to an affinity reagent such as the paralogs described in U.S. Pat. No. 4,963,263 incorporated herein by reference.

In addition to reactivity through specific binding, any type of reactivity can be measured. For example, if the candidate analytes are a series of isoenzymes, the effect on activity of each of a panel of inhibitors could be measured, or the level of activity with regard to a series of substrates could be measured. Conversely, if the analyte panel is a series of related substrates, reactivity of a series of enzymes with these related substrates can be used to determine the profile. It is not necessary that the same type of reactivity or other characteristic parameter be used to determine a value for each information channel of which the profile is comprised. Thus, the profile may constitute a combination of binding with an antibody, binding with an inhibitor, reactivity with an enzyme, reactivity with a substrate, or any other chemical activity or physical characteristic which has a variable value for the various candidate analytes to be determined.

Similarly, the choice of specific assay format which detects the reactivity of the reagents in the panel or value of characteristic parameter in the panel that provides the series of information channels for the profiles of the analyte group members is optional. Binding or other reactivity of the sample to be tested and the production of a standard set of data points for various analyte compositions can be determined in either a direct or competitive format. For example, a binding agent can be labeled and the binding to antigen detected by precipitating the resultant complex and determining the amount of label in the precipitate. Alternatively, and more conveniently, a binding reagent is coupled to a solid support and the candidate analyte allowed to compete with a similar analyte of known binding capacity. Additional methods for conducting assays designed to detect and measure binding of a specific binding reagent to the analytes in a particular group are disclosed in PCT application US88/03554, and incorporated herein by reference. Methods for design of specific binding reagents are also found in U.S. Pat. No. 4,963,263 and in PCT US89/01194 and PCT US90/06333, all incorporated herein by reference. Alternative protocols will be immediately apparent to practitioners of immunoassays or other specific binding assays.

Similarly, methods to determine parameters which measure chemical reactivity or physical characteristics are also readily devised. For example, the relative mobilities of the analytes in a chromato-graphic support constitutes a differential cross-reactivity to provide information for one channel. Electrophoretic mobilities, pI values, reactivity with particular substrates or inhibition by particular inhibitors also constitute parameters which provide information for the profile.

However the value of the characteristic parameter for each information channel is determined, a profile for a panel of "cross-reactive" characteristic parameters is determined for a series of known analyte compositions. The simplest such compositions, and those typically used to obtain the standard pattern, are samples containing only single member analytes at a range of concentrations. The standard plot ultimately obtained from these control data points permits detection of single analytes by correlation with known positions. Calculation of plot positions for mixtures permits their identification by similar matching.

The profiles determined for the analytes, standards, and unknown compositions are somewhat analogous to cross-reaction immunoassay (CRIM) profiles and the method of the invention is analogous to comparing the CRIM profile of a sample to be tested with a predetermined plot of CRIM profiles obtained from samples of known analyte composition. In the invention method, the concept of a CRIM profile is broadened to include a series of channels of values of characteristic parameters such as specific reactivities which include not only reactivities with antibodies or binding agents, but also reactivity in a variety of contexts and any informational physical or chemical characteristic which has a differential value across the candidate analytes. For convenience, because the number of characteristics which could be surveyed is large, this profile is designated herein a survey of characteristics profile or "SC profile."

Thus, by "SC profile" is meant a pattern of values of characteristic parameters across a panel of information channels provided by reagents or a set of physical or chemical characteristics with respect to a single fixed analyte composition. In a typical SC profile useful in the invention, the characteristics of the analyte with respect to 2–10 preferably 4–6 different information channels are compiled. For example, the reactivity of a sample with a panel of 2–10, preferably 4–6, different reagents can be determined. As will be apparent from the example below, each composition will have a characteristic SC profile across the panel of information channels comprised of reactivity with reagents and/ or other characteristics. Larger numbers of members of the panel provide greater refinement of the assay; smaller numbers of members of the panel are more convenient. The choice of the number of members of the panel is arbitrary, depending on the level of fine tuning desired in the assay; the mathematical techniques disclosed herein permit selection of the most meaningful panel members and can be used to reduce the number of information channels needed in the profile.

If the profiles are to be used to determine concentration, however, at least some of the characteristics which are set forth in the information channels must be dependent on concentration of the candidate analyte. Therefore, for use in such concentration determinations, specific binding to receptors, antibodies, or other specific binding reagents is especially useful. However, substrate reactivity with enzymes, inhibition of enzymes by competitive inhibitors, and other reactivities which are concentration-dependent can also be used.

In obtaining the profiles at various concentrations, the simplest conceptual approach provides this series of profiles by direct measurement of the inhibition values at various known analyte concentrations with respect to binding reagents or enzymatic activity. However, additional profiles can be interpolated using the curves obtained by plotting % inhibition vs. analyte concentration.

Mathematical Processing

The profiles obtained for the individual standard compositions to be compared to unknown samples are then subjected to computational techniques which permit the comparison of the standard profiles with those of unknowns, a process not readily performed by hand.

In the simplest form of application of these pattern recognition techniques, each SC profile is plotted as a point in n dimensions, wherein n is the number of binding agents in each panel.

For example, one might use a panel containing six different binding agents which are monoclonal antibodies. These antibodies are assumed to be cross-reactive with, for example, ten members of a class of analytes $A_i$ wherein A represents the analyte and i is an integer of 1–10. One of these analytes, $A_1$, for example, might be chosen as a labeled competitor to determine profiles of competition for binding at various concentrations of itself and of the remaining analytes. Using a set concentration of labeled $A_1$, the percent inhibition, for example, is determined with respect to binding each antibody in the panel at various concentrations of $A_1$–$A_{10}$.

For each analyte, $A_i$, at one concentration, then, there are six data points which are percentages of inhibition with respect to labeled $A_1$ for binding to the various antibodies in the panel. These percentages are then treated mathematically as defining the location of a single point in six-dimensional space where the first dimension describes the percent inhibition with respect to the first antibody, the second dimension describes the percent inhibition with respect to the second antibody, and so forth. Points are thus determined representing the various concentrations of $A_1$, $A_2$, $A_3$ . . . $A_{10}$.

As a six-dimensional plot is not readily visualized, known mathematical techniques, such as those described by D. L. Massart, et al., "Chemometrics: A Textbook" (1988) Elsevier, (N.Y.), can be used to project the six-dimensional array onto a two-dimensional surface or other surface of lower dimensionality. This series of points in two-dimensional space can then be used to visualize comparisons of the profile obtained using an unknown sample with the profiles of standards to identify the composition of the sample. Of course, as the six-dimensional space can be handled mathematically, there is no requirement for the projection in order to match the data point generated by the samples with those in the set of reference points.

Choosing a projection does, however, provide the additional benefit of rank ordering the antibodies with respect to their utility for SC. The more nearly perpendicular the projection plane is to an axis in the six dimensional space, the greater is the loss of that component's information content in the projection. Since factor analysis generates an optimal plane for preserving the scattering aspect of that information, the relative importance of the antibodies in this regard is readily determined. This knowledge may be usefully applied, for example in reducing the number of antibodies in the panel.

In the example described below, it was found that reliable estimates could be obtained for compositions of an unknown sample in about 85% of the cases using this rather simple mathematical approach. Improved results were obtained by applying methods to distinguish between data points which are of significance from those which are relatively meaningless.

In effect, weighting factors for the various members comprising the profile can be introduced to account for the fact that those concentrations which represent inhibition of binding on the linear part of the standard curve are more informative than those in the asymptotic parts of the curve at very low or high inhibition. These factors are applied when the data are treated by "variance analysis." In this technique, in general outline for this example, the value represented by the dimension corresponding to each of the six monoclonal antibodies in the panel is compared separately with the corresponding value for the corresponding antibody in the unknown sample, rather than as a totality of the n-dimensional result for all six antibodies.

For example, the observed inhibition value for antibody #1 implies a corresponding concentration for analyte $A_1$, and a different corresponding concentration for analyte $A_2$, etc. Antibody #2 similarly generates a family of predictions, and so forth. For the correct choice of analyte, the individual predictions of the six antibodies will agree more closely than for an incorrect choice of analyte. This approach to profile identification is a form of variance analysis, normally used to compare independent estimates made in different laboratories or methods of determination. Calculation of variances can be easily modified to weight the predictions by a factor representing the reliability of the data, as judged by the variance in the data set used to construct the standard curve. This procedure is referred to herein as "weighting the results."

This mathematical technique, as described by Mandel, "The Statistical Analysis of Experimental Data" (1984) Dover, provided sufficient weighting of the significant binding data to provide a clear result in 95% of the cases.

Finally, neural net systems can also be used, wherein adjustment factors arise implicitly in the process of training the net's input/output characteristics using standards. The systems are outlined, for example, in Hartz, J. A., et al., *Introduction to the Theory of Neural Computation* (Addison Wesley, Santa Fe Institute Series on Complex Systems, 1991); *Parallel Distributed Processing*, 2 vols. (D. E. Rumelhart and J. L. McClelland, eds., MIT Press, 1986); or *DARPA Neural Network Study* (Armed Forces Communication and Electronics Association Int'l Press, 1988).

The high reliability of analyte identification achieved through the use of small panels of binding agents that have only moderate intrinsic specificity for the compounds is unexpected from prior art binding assays wherein enormous effort has been expended to achieve higher intrinsic specificity. The method of the Invention is thus useful not only for improving the reliability of existing assays, but also for extending the scope of immunoassay technology by facilitating the isolation of suitable antibodies, for example, from recombinant libraries.

Packaged Assays

The reagents and software for use in the assays of the invention could conveniently be packaged to permit rapid and convenient assay of complex samples in situations where various members of a class of compounds may be present, such as in those situations set forth above. A typical kit for such an assay where binding reagents are used would include the members of a panel of reagents, preferably coupled to a solid support, along with labeled competitor and a means for detection of the label. Suitable labels include radioactive isotopes, fluorescence emitters, and enzymes. Alternatively, the binding agents, such as antibodies, may be supplied in labeled form and a competitive analyte linked to solid support. For direct conduct of the assay, a sandwich format could be used wherein antibody-coated solid supports are reacted with sample and then treated with a second antibody bearing label.

The selection of reagents and accessory materials for the kit will, of course, depend on the choice of characteristics used to construct the SC profile. If reactivity with respect to various substrates or the effect of various inhibitors is utilized, for example, the kit will include the candidate substrates, candidate inhibitors, and means for detection of reaction.

The values obtained in the reaction of the reagent panel with the sample are then compared to the reference data bank. Software supplied with the packaged reagents permits entry of the relevant results obtained from the sample and comparison to the reference panel. The nature of the software will depend on the particular mathematical processing selected, as described above.

The following example is intended to illustrate, but not to limit, the invention.

Preparation A

Production of Monoclonal Antibodies

Two s-triazine compounds, atrazine and simazine (see Preparation B) were conjugated to keyhole limpet hemocyanin (KLH) using NHS and EDCI (Pierce Chemical Company, Rockford, Ill.) and used to immunize mice, as described by Goodrow, M., et al., *J Agric Food Chem* (1990) 38:990–996. When high titers of anti-s-triazine antibodies were obtained, the mice were sacrificed and the spleen cells were recovered. Fusions of the spleen cells with murine myeloma cells in 50% polyethylene glycol yielded hybridomas which were screened for antibody production using an ELISA assay for binding to immobilized atrazine bovine serum albumin (BSA) conjugates. These conjugates were prepared using a carbodiimide-based protocol.

Positive cultures were cloned by limiting dilution and stable cell lines were cultured in complete medium with 5% fetal bovine serum. Culture supernatants were collected, aliquoted and stored frozen at −20° C.; antibody IgG subtypes were determined using an isotyping kit from Zymed. A panel of 5 monoclonal antibodies reactive at various affinities with seven important s-triazine derivatives were selected. These are AM5C5.3, AM1B5.1, AM5D1.2, and AM7B2.1 from the atrazine immunization and SA5A1.1 from the simazine immunization.

Preparation B

Antigen/Analyte Compositions

A set of 7 triazine analogs was used to illustrate the invention technique. The structures of these analogs, which are commercially available, are shown in Table 1.

TABLE 1

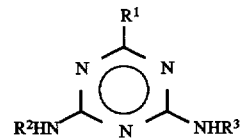

| Triazine Analogs | $R^1$ | $R^2$ | $R^3$ |
| --- | --- | --- | --- |
| 1. Atrazine | Cl | Isopropyl | Ethyl |
| 2. Simazine | Cl | Ethyl | Ethyl |
| 3. Propazine | Cl | Isopropyl | Isopropyl |
| 4. Prometon | O-Methyl | Isopropyl | Isopropyl |
| 5. Prometryne | S-Methyl | Isopropyl | Isopropyl |
| 6. Ametryne | S-Methyl | Ethyl | Isopropyl |
| 7. Terbutryne | S-Methyl | t-Butyl | Ethyl |

For conjugation to BSA or KLH via carbodiimide-mediated crosslinking the ethyl group at $R^3$ in atrazine is replaced by $-(CH_2)_5COOH$ and the chloro group for simazine at position $R^1$ is replaced by $-SCH_2CH_2COOH$.

In general, conjugation is to a different carrier for immunization and for screening. This minimizes detection of antibodies in the screen which are raised against the carrier, rather than the desired hapten.

EXAMPLE 1

Determination of Antibody Specificity

Five monoclonal antibodies obtained as described in preparation A were tested for reactivity with respect to the seven analytes of preparation B. This profiling was conducted using an ELISA format in 96-well microplates. The plates were coated overnight at 4° C. with an atrazine-BSA conjugate. Extraneous protein-binding sites were blocked by 2-hour incubation with 0.5% each of BSA and casein, followed by washing with PBS-Tween (10 mM Na phosphate, pH 7.2, 100 mM NaCl plus 0.05% Tween-20).

The antibody to be tested plus varying concentrations of the s-triazine analog to be tested in assay buffer (PBS/Tween plus 0.1% each BSA and casein) were added to the plate in quadruplicate wells. The plates were incubated at room temperature for 2 hours. Bound antibody was quantitated using a secondary alkaline phosphatase-labeled goat anti-mouse IgG (1:1000) with p-nitrophenol phosphate as substrate (1 mg/ml in 0.1M diethanolamine, pH 10.3; 0.5 mM $MgCl_2$). Endpoint accumulation of reaction product was determined by measuring absorbance at 405 nm with a $V_{max}$ microplate reader (Molecular Devices, Menlo Park, Calif.). Inhibition curves were fitted using the Four-Parameter Logistic Program in the software package Soft Max (V.2.01C, Molecular Devices). The reduction in binding of the monoclonal antibodies to the solid phase due to the presence of the s-triazine analog at a particular concentration was expressed as a percentage of optical density of the zero-dose control (R/Ro×100%).

Figure 1B:
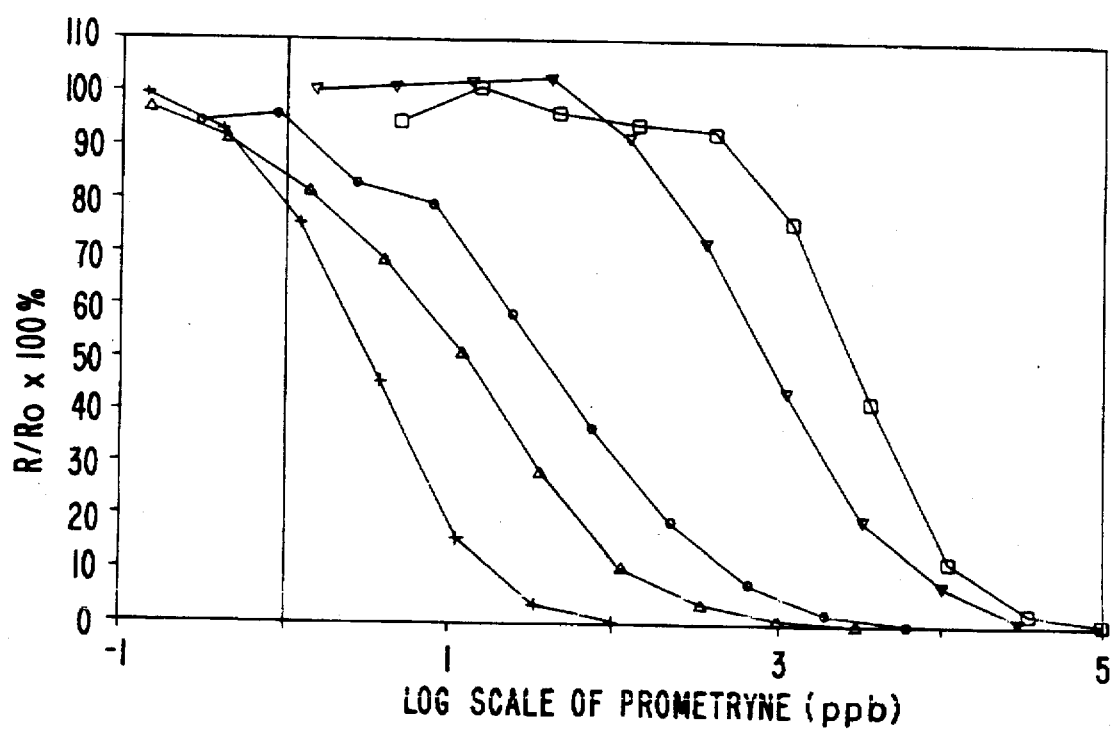
Figure 2A:
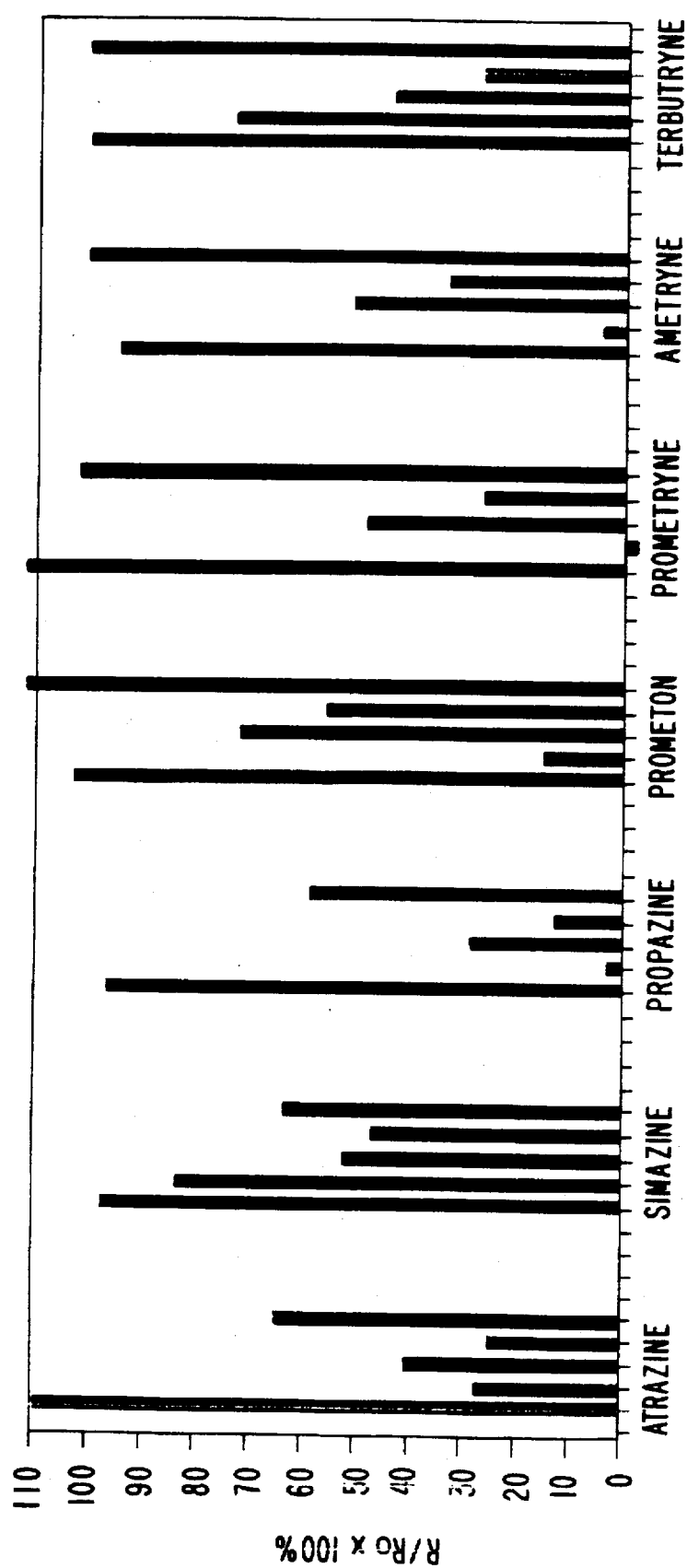
FIG. 2(A) and 2(B) show predicted and experimental survey of characteristic (SC) profiles for triazine homologs determined at 50 parts per billion (ppb).

Typical results for atrazine and prometryne are shown in FIG. 1A and B, respectively. As shown in the figure, the inhibition curves over the panel are different for the two analogs. The $IC_{50}$ values (the concentration at which 50% inhibition was obtained) are displayed for all seven analogs against the 5-member antibody panel in Table 2.

curves obtained for each of the analogs as exemplified in FIG. 1. The result of this theoretical calculation for 50 ppb is shown in FIG. 2A. As seen, the percentage inhibition patterns across the panels is distinctive for each individual analog.

Figure 2B:
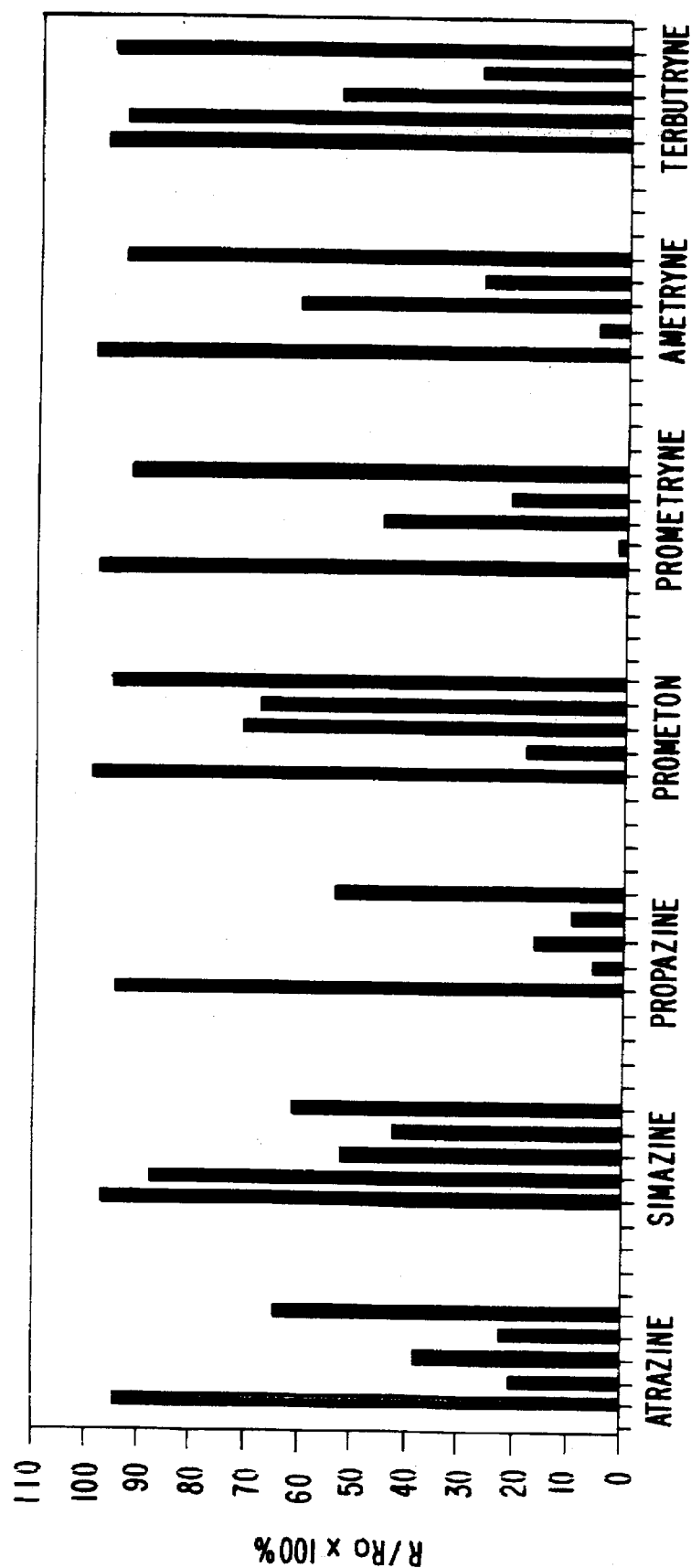

The profiles were also determined experimentally at 50 ppb, as shown in FIG. 2B. The calculated and experimental patterns are highly similar. The results shown graphically in FIG. 2B are given as numerical values in Table 3 below.

Matching experimental profiles to calculated reference profiles allows identification of unknown samples. A catalog of calculated profiles thus provides a reference for unknown sample determination.

TABLE 2

Anti-Triazine Mabs and Their Relative Specificities Against Seven S-Triazines

| Cell Line* | IgG Subtype | | IC50 (ppb)** | | | | | | |
|---|---|---|---|---|---|---|---|---|---|
| | | | Atrazine | Simazine | Propazine | Prometon | Prometryne | Ametryne | Terbutryne |
| AM5C5.3 | IgG 2b | K | 555.0 | 884.0 | 596.0 | 9700.0 | 3030.0 | 1790.0 | 1330.0 |
| AM1B5.1 | IgG 1 | K | 15.5 | 273.0 | 6.7 | 18.4 | 3.2 | 6.6 | 494.0 |
| AM5D1.2 | IgG | K | 29.6 | 56.5 | 7.7 | 176.0 | 42.8 | 92.8 | 61.0 |
| AM7B2.1 | IgG 2b | K | 14.1 | 38.7 | 5.4 | 114.0 | 13.0 | 18.6 | 19.4 |
| SA5A1.1 | IgG 1 | K | 74.0 | 83.1 | 60.0 | 2100.0 | 870.0 | 1200.0 | 1190.0 |

*The first two letters of each clone designate whether the immunizing hapten was atrazine-mecaptopropanoic acid (AM) or simazine-aminohexanoic acid (SA) conjugates.
**IC50 is the concentration of free triazine that half-maximally inhibited the competition ELISA. Values determined from four parameter fitted curves; ppb = parts/billion or ng/ml.

These results show that each triazine analog has a characteristic profile with respect to the 5-member antibody panel.

TABLE 3

IMMUNO-CROSSREACTION PROFILES OF
7 S-TRIAZINES (AT 50 PPB) VS. 5 ANTI TRIAZINE MABS
Activities are expressed as percent of zero-dose
control +/− standard deviation (n = 3)

| | AM5C5.3 | AM1B5.1 | AM5D1.2 | AM7B2.1 | SA5A1.1 |
|---|---|---|---|---|---|
| ATRAZINE | 89.7 +/− 6.8 | 9.6 +/− 2.9 | 28.1 +/− 1.9 | 11.7 +/− 0.9 | 64.8 +/− 2.3 |
| SIMAZINE | 88.2 +/− 5.5 | 75.5 +/− 6.1 | 43.6 +/− 2.8 | 26.3 +/− 2.4 | 63.6 +/− 4.9 |
| PROMETRYN | 109.8 +/− 4.6 | 0.9 +/− 1.3 | 47.9 +/− 3.0 | 18.9 +/− 1.3 | 59.4 +/− 4.9 |
| PROMETON | 103.6 +/− 4.7 | 17.8 +/− 2.4 | 71.6 +/− 1.5 | 46.6 +/− 1.4 | 105.1 +/− 4.6 |
| PROPAZINE | 83.8 +/− 6.1 | 1.4 +/− 0.8 | 14.7 +/− 2.1 | 3.9 +/− 0.6 | 102.7 +/− 3.0 |
| AMETRYN | 91.8 +/− 1.8 | 6.2 +/− 1.1 | 44.0 +/− 2.4 | 27.0 +/− 1.0 | 100.9 +/− 3.8 |
| TERBUTRYN | 96.6 +/− 2.4 | 80.6 +/− 5.6 | 41.5 +/− 4.3 | 20.1 +/− 1.3 | 101.1 +/− 4.8 |

EXAMPLE 2

Determination of SC Profiles

A series of standard profiles for each triazine analog over the 10–1000 ppb range was calculated from the inhibition Determination of Composition/Reactivity Plot Profiles such as those shown in FIG. 2A of Example 2 were determined for a series of concentrations of all seven triazines in the 10–1000 ppb range. The percent inhibition values for the five antibodies for each triazine at each concentration provides a coordinate in 5-dimensional space. Thus, each analog at each concentration gives a single point representing the profile in 5-dimensional space.

The resultant pattern shows a unique series of points represented by individual analytes at various concentrations with respect to the antibody panel.

Figure 3:
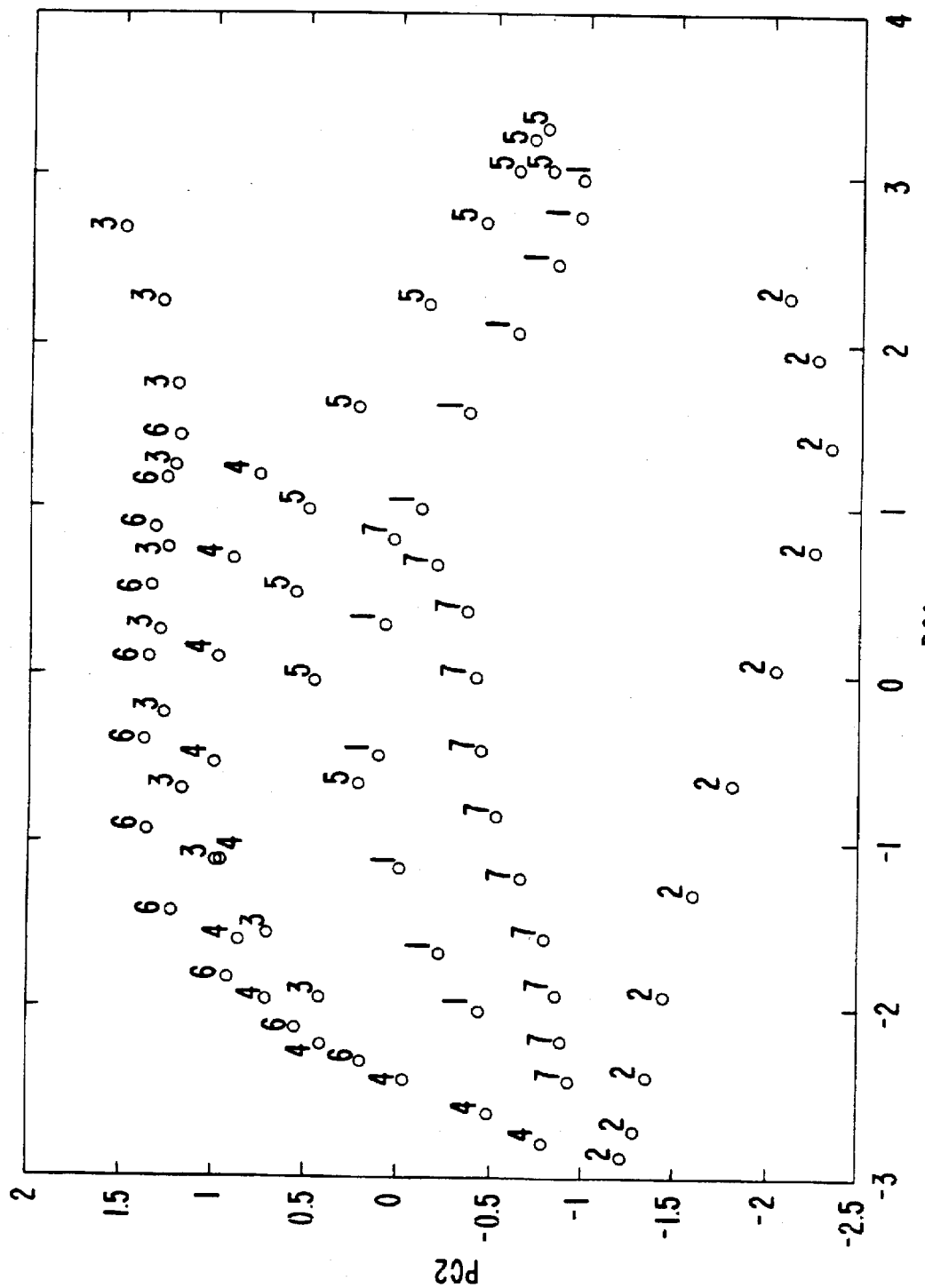
FIG. 3 shows an optimized two-dimensional projection of five-dimensional SC profiles for seven triazine herbicides at concentrations ranging from 10–1000 ppb.

In order to visualize these data better, the 5-dimensional plot is projected into a 2-dimensional array, as shown in FIG. 3.

The orientation of the two-dimensional plane used for this projection is that which best preserves the scatter of the data, i.e., which minimizes points lying on top of each other in the projection when they are well separated. This orientation is defined mathematically as the plane specified by the principal components of the data. Projecting points onto the plane defined by the principal components preserves the clustering and characteristics of the original data as described by Massart, D. L., et al., "Chemometrics: A Textbook" (1988) Elsevier, N.Y.

As shown in FIG. 3, all points labeled "1" represent various concentrations of atrazine, all points labeled "2" represent varying concentrations of simazine, and so forth.

By determining the point location resulting from obtaining the profile of a sample in the same manner as described for known compositions in this example, the analyte composition of the sample can be obtained.

We claim:

1. A method to determine the analyte composition of a sample containing at least one member analyte of a set of candidate analytes, which method comprises:

contacting the sample with at least two specifically reactive reagents for which each member of the set is differentially cross-reactive;

detecting and measuring the amount of reactivity of each of said reagents with the sample, each measurement determining a value for a characteristic parameter for the sample;

compiling said values to obtain a survey of characteristics (SC) profile for the sample;

comparing the SC profile obtained from the sample with a reference set of SC profiles obtained from known compositions of the members of the set of candidate analytes; and identifying the analyte composition of the sample based on said comparing of SC profiles.

2. The method of claim 1 wherein said comparing includes the steps of:

determining a position for the point obtained by plotting the values obtained for the sample in n-dimensional space, wherein n is the number of said reagents; and specifically comparing the position of said point to predetermined points in said n-dimensional space representing various known concentrations of said member analytes reacted with said reagents, thereby determining the analyte composition of the sample.

3. The method of claim 2 wherein said reference set of SC profiles includes the value of the concentration of candidate analytes corresponding to the value of each characteristic parameter so as to obtain a set of determined concentrations for each candidate analyte.

4. The method of claim 3, wherein said identifying step further includes the step of weighting the results for each characteristic parameter proportional to the reliability of the data.

5. The method of claim 1 wherein at least one of said specifically reactive reagents is not an antibody.

6. The method of claim 5 wherein said at least one measurement of reactivity is based upon the interactions of enzyme to substrate, enzyme to inhibitor, ligand to receptor or binding to a paralog.

7. The method of claim 1 wherein said comparing includes providing the resultant for each characteristic parameter in each SC profile to a neural net which contains the reference set of SC profiles.

8. The method of claim 1 wherein said cross-reactive set of analytes contains 2–20 members, and/or said characteristic parameters contains 2–10 characteristic parameters.

9. The method of claim 2 wherein said specifically reactive reagents are antibodies or immunologically reactive fragments thereof, and wherein said antibodies are single chain antibodies or recombinantly produced antibodies.

10. The method of claim 1 wherein said cross-reactive set of analytes is comprised of triazines.

11. A method to prepare a reference set of SC profiles with respect to members of a cross-reactive set of analytes, which method comprises:

contacting each member of the set with n specifically reactive reagents for which each member of the set is differentially cross-reactive, and wherein n is at least 2;

detecting and measuring the amount of reactivity of each of said reagents with each member of the set to determine a value for a characteristic parameter for each member of the set, wherein each value constitutes an information channel;

determining the value of each characteristic parameter in each information channel for each member of said cross-reactive set of analytes at a series of concentrations of said member to obtain an SC profile of said member at each such concentration; and storing said SC profiles in a computationally accessible form.

12. The method of claim 11 wherein said computationally accessible form is a pattern of points in n-dimensional space useful for the determination of analyte composition of a sample containing at least one member analyte of a cross-reactive set of analytes obtained by identifying the points obtained by plotting the values of the characteristic parameters for each concentration of analyte with respect to each of n characteristic parameters in n-dimensional space;

thus obtaining said pattern of points representing known analyte concentrations in n-dimensional space.

13. The method of claim 12 which further comprises projecting said pattern into a lower-dimensional space to obtain a more computationally tractable representation of said known concentrations.

14. The method of claim 11 wherein said characteristic parameters comprise reactivity with said specifically reactive reagents for members of said cross-reactive set of analytes, and wherein said determining the value of each characteristic parameter comprises detecting the reactivity of each specifically reactive regent for each member of said cross-reactive set of analytes at a series of concentrations of said member.

15. The method of claim 14 wherein

A) the step of detecting the reactivity of each specifically reactive reagent for each member of said cross-reactive set of analytes at said series of concentrations is conducted by:

contacting a plurality of samples with different known concentrations of member analytes of said cross-reactive set with each of n specifically reactive reagents; and detecting and measuring the amount of reactivity of each specifically reactive reagent in the panel with the samples containing said known concentrations, or wherein B) the step of detecting the reactivity of each specifically reactive reagent for each member of said cross-reactive set of analytes at a series of concentrations of said member is conducted by:

calculating a measure of said reactivity at each concentration from an inhibition curve for said analyte with respect to said specifically reactive reagent.

16. The method of claim 10 wherein the specifically reactive reagents are antibodies or immunologically reactive fragments thereof, and wherein the antibodies are single chain antibodies or recombinant antibodies.

17. The method of claim 11 wherein said set of cross-reactive analytes are triazines.

18. A method to determine the analyte composition of a sample containing a plurality of member analytes of a set of candidate analytes, wherein each member of the set has a differential value for a characteristic parameter associated with a given assay of reactivity, chemical activity or physical properties, which method comprises:

contacting the sample with at least two specifically reactive reagents for which each member is differentially cross-reactive to determine a value for a characteristic parameter with respect to each of said specifically reactive reagents, wherein each value constitutes an information channel and at least one of said specifically reactive reagents reacts by means of specific binding;

compiling said values to obtain a survey of characteristics (SC) profile for the sample;

comparing the SC profile obtained from the sample with a reference set of SC profiles obtained from known compositions of the members of the set of analytes; and identifying the analyte composition of the sample based on said comparing of SC profiles.

19. The method of claim 18 wherein at least one of said specifically reactive reagents is not an antibody.

* * * * *